United States Patent
Falahee

(10) Patent No.: US 8,574,266 B2
(45) Date of Patent: *Nov. 5, 2013

(54) PERCUTANEOUS FACET FIXATION SYSTEM

(75) Inventor: Mark H. Falahee, Ann Arbor, MI (US)

(73) Assignee: US Spine, Inc., Salt Lake City, UT (US)

( * ) Notice: Subject to any disclaimer, the term of this patent is extended or adjusted under 35 U.S.C. 154(b) by 579 days.

This patent is subject to a terminal disclaimer.

(21) Appl. No.: 12/550,017

(22) Filed: Aug. 28, 2009

(65) Prior Publication Data

US 2009/0318980 A1    Dec. 24, 2009

Related U.S. Application Data

(63) Continuation of application No. 10/683,076, filed on Oct. 10, 2003, now Pat. No. 7,608,094.

(60) Provisional application No. 60/417,543, filed on Oct. 10, 2002.

(51) Int. Cl.
*A61B 17/70* (2006.01)
*A61B 17/04* (2006.01)
*A61B 17/86* (2006.01)
*A61F 2/08* (2006.01)

(52) U.S. Cl.
USPC .................................. 606/247; 606/305

(58) Field of Classification Search
USPC ......... 606/86 R, 99, 104, 116, 117, 205, 220, 606/247, 301, 305; 81/347, 352; 269/3, 6, 269/95
See application file for complete search history.

(56) References Cited

U.S. PATENT DOCUMENTS

| | | | |
|---|---|---|---|
| 1,412,961 A | 4/1922 | Periolat | |
| 5,527,312 A | 6/1996 | Ray | |
| 5,558,674 A | 9/1996 | Heggeness et al. | |
| 6,019,759 A * | 2/2000 | Rogozinski | 606/308 |
| 6,257,565 B1 | 7/2001 | Houston et al. | |
| 6,355,038 B1 * | 3/2002 | Pisharodi | 606/300 |
| 6,485,518 B1 | 11/2002 | Cornwall et al. | |
| 6,540,747 B1 | 4/2003 | Marino | |
| 6,592,587 B1 * | 7/2003 | Roger | 606/318 |
| 6,648,893 B2 | 11/2003 | Dudasik | |
| 6,669,698 B1 | 12/2003 | Tromanhauser et al. | |
| 6,706,048 B2 | 3/2004 | Hermann et al. | |
| 6,755,834 B2 * | 6/2004 | Amis | 606/916 |
| 6,811,567 B2 | 11/2004 | Reiley | |
| 6,949,123 B2 | 9/2005 | Reiley | |
| 6,966,930 B2 | 11/2005 | Arnin et al. | |
| 7,041,136 B2 | 5/2006 | Goble et al. | |
| 7,060,068 B2 | 6/2006 | Tromanhauser et al. | |
| 8,206,400 B2 | 6/2012 | Falahee | |
| 2004/0111093 A1 | 6/2004 | Chappuis | |
| 2004/0225360 A1 | 11/2004 | Malone | |
| 2004/0254575 A1 | 12/2004 | Obenchain et al. | |
| 2005/0124993 A1 | 6/2005 | Chappuis | |
| 2005/0149030 A1 | 7/2005 | Serhan et al. | |
| 2005/0273110 A1 | 12/2005 | Boehm, Jr. et al. | |
| 2006/0004367 A1 | 1/2006 | Alamin et al. | |
| 2006/0111779 A1 | 5/2006 | Petersen | |
| 2006/0111780 A1 | 5/2006 | Petersen | |

* cited by examiner

*Primary Examiner* — Anu Ramana
(74) *Attorney, Agent, or Firm* — Phillips Ryther & Winchester; Matthew D. Thayne

(57) ABSTRACT

A percutaneous facet fixation system minimally invasive, reproducible, efficient, and effective. Capable of immediate stabilization of a facet joint complex, the instrumentation and methods may be used with C-arm and/or endoscopic visualization.

13 Claims, 3 Drawing Sheets

PERCUTANEOUS FACET FIXATION SYSTEM

REFERENCE TO RELATED APPLICATIONS

This application is a continuation of U.S. patent application Ser. No. 10/683,076, filed Oct. 10, 2003, which claims priority from U.S. Provisional Patent Application Ser. No. 60/417,543, filed Oct. 10, 2002, the entire content of both of which is incorporated herein by reference.

FIELD OF THE INVENTION

This invention relates generally to spine surgery and, in particular, to a percutaneous facet fixation system.

BACKGROUND OF THE INVENTION

For patients with a high degree of spinal instability (e.g. fractures), or in revision surgery, a combination anterior/posterior fusion is indicated at one or more levels. Fusing both the front and back provides a high degree of stability for the spine and a large surface area for the bone fusion to occur. The disc may be approached either as an anterior lumbar interbody fusion (ALIF), or as a posterior lumbar interbody fusion (PLIF). Both procedures are well known to those of skill in the art.

To further stabilize vertebral segments, posterior instrumentation is often performed in conjunction with an interbody fusion. The most commonly used posterior instrumentation system in use today is pedicle screw fixation. The major disadvantage to this technique is the necessity of major muscle dissection, which can lead to morbidity and scarring.

Facet screw fixation offers the advantage of placing a single screw across each articulating facet joint to immobilize a motion segment, thereby reducing the amount of hardware (and therefore exposure) necessary. Existing techniques, however, still demand relatively open procedures, such that the need remains for a facet fixation system compatible with minimally invasive surgical (MIS) procedures.

SUMMARY OF THE INVENTION

The present invention is a percutaneous system of facet fixation that is minimally invasive, reproducible, efficient, and effective. Capable of immediate stabilization of a facet joint complex, the instrumentation and methods may be used with C-arm and/or endoscopic visualization.

DETAILED DESCRIPTION OF THE INVENTION

Figure 1:
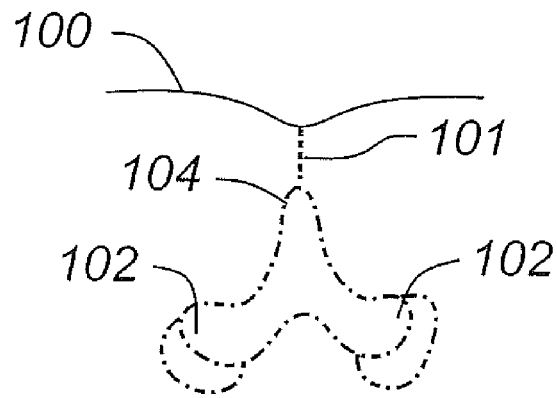
FIG. 1 is a highly-simplified drawing that shows the facet joints of a patient to which this invention is applicable.

Reference is now made to the drawings, wherein FIG. 1 is a highly-simplified drawing that shows the facet joints 102, 102' of a patient 100 to which this invention is applicable. The proximal spinous process is indicated at 104. The patient is placed in a prone position under general anesthetic. A C-arm is preferably utilized to determine fixation level and approach for incision.

Figure 2:
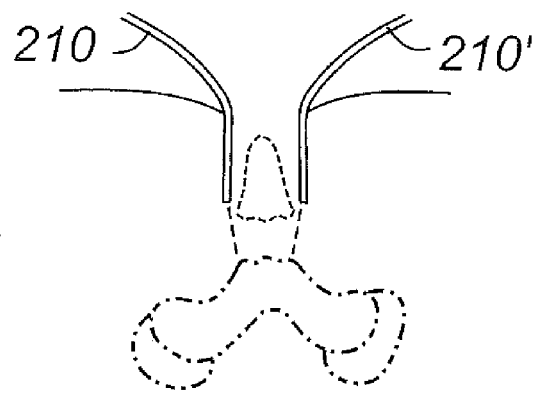
FIG. 2 is a drawing showing a posterior approach to the spine using retractors and removal of the spinous process to the junction to the lamina.

A 1.0-inch incision 101 (or thereabouts) is made in midline over the proximal spinous process 104. (For L4-L5 fixation, the incision made over L4 spinous process.) As shown in FIG. 2, the spinous process removed to junction of lamina, allowing access angle to facet joints bilaterally.

Figure 3:
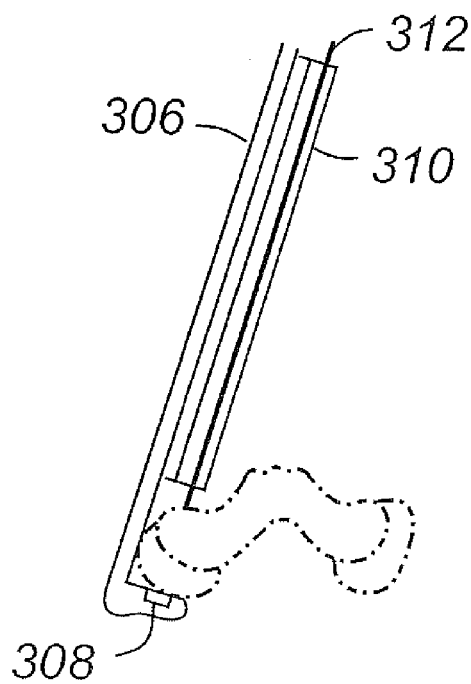
FIG. 3 is a drawing that shows a guide wire passed by C-arm or endoscopic guidance to a facet joint in conjunction with the lower arm of the facet gun.

FIG. 3 is a drawing that shows the way in which a guide wire 312 is passed by C-arm or endoscopic guidance to a facet joint in conjunction with the lower arm of a facet gun 306 according to the invention. The lower arm of facet gun contains a deep locking nut 308 abutting lateral surface of the superior facet (L5). The deep locking nut is positioned in alignment with the guide wire 312 by C-arm past the facet joint.

Figure 4:
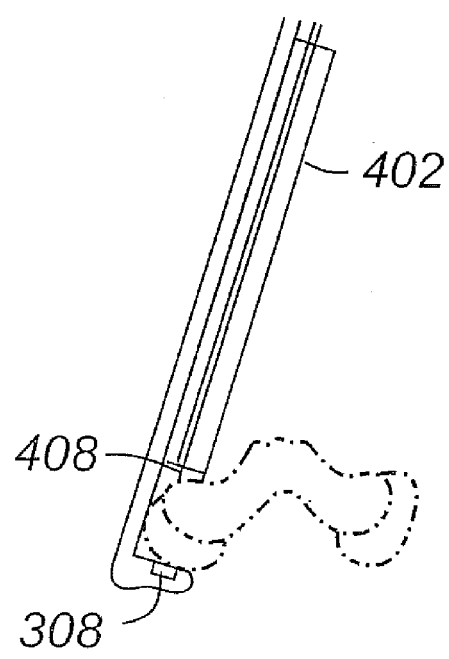
FIG. 4 is a drawing that shows the upper arm of the facet gun, including a locking nut, inserted along the track of the guide wire of FIG. 3.
Figure 5:
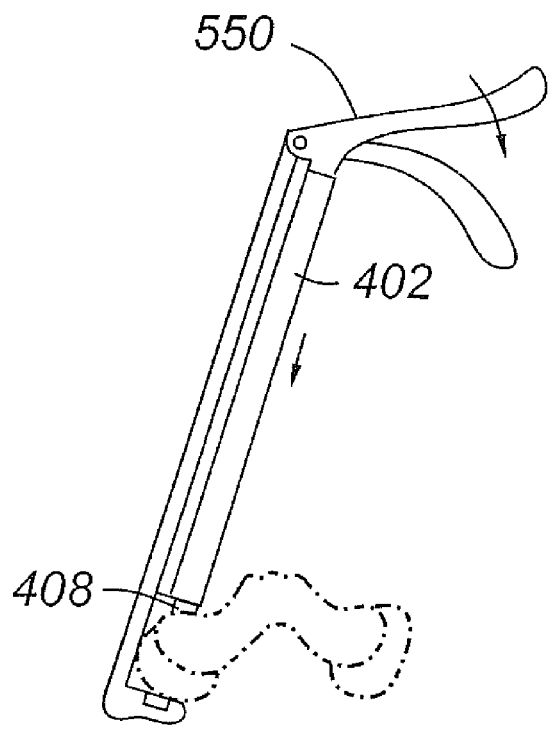
FIG. 5 shows the handle of a facet gun compressed, locking the nuts onto the upper and lower surfaces of the facet joint.

FIG. 4 is a drawing that shows the upper arm of the facet gun 310, including a locking nut 408, also inserted along the track of the guide wire of FIG. 3. The superficial locking nut 408 is inserted over the guide sleeve of lower arm, making contact with surface of inferior facet. As shown in FIG. 5, the handle of the facet gun compressed, holding the nuts 408, 308 onto upper and under surface of facet joint.

Figure 6:
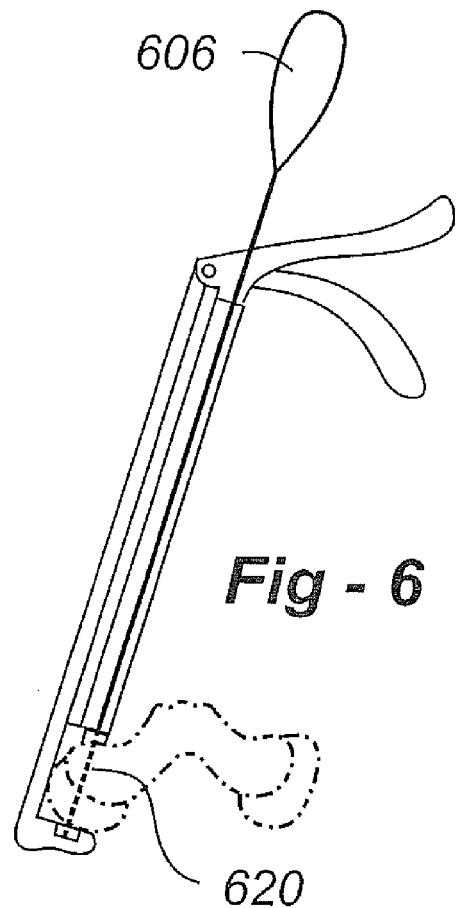
FIG. 6 shows how a bolt is driven through the superficial and deep nuts, thereby fusing the facet joint.
Figure 12:
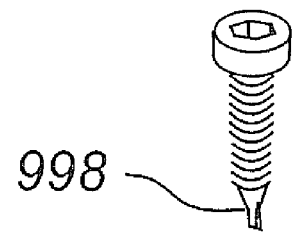
FIG. 12 is a drawing of a bolt including a drill bit tab useful to the invention.

Referring to FIG. 6, a previously selected facet bolt, preferably with drill bit head 998 as shown in FIG. 12, is inserted into barrel of upper facet gun sleeve. The bolt is driven through superficial and deep nuts using a manually operated tool 606, passing through facet joint, locking into the superficial nut and compressing the joint together.

Figure 7:
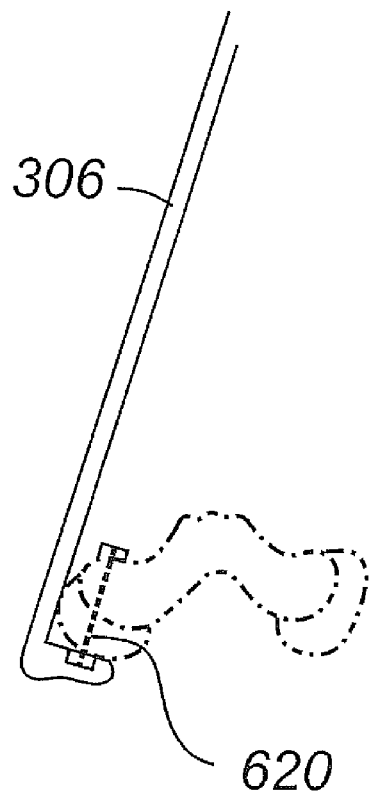
FIG. 7 shows the fused joint with the lower arm of the facet gun still in position.
Figure 8:
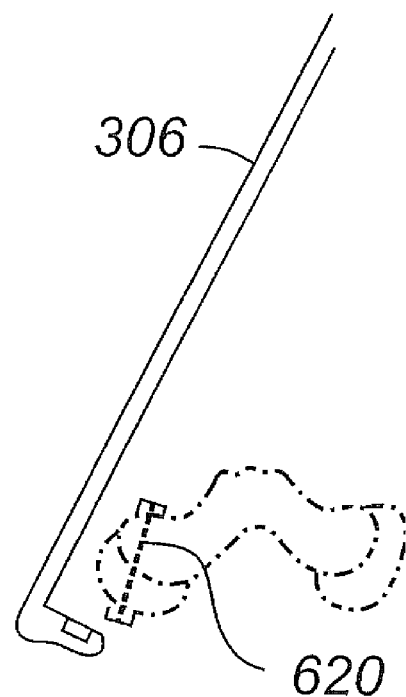
FIG. 8 shows the removal of the lower arm.

The upper arm of facet gun is disengaged in FIG. 7. The lower arm is pushed deeper, disengaging itself from the deep nut, and the arm and guide wire are removed as shown in FIG. 8. The procedure is then repeated for opposite side.

Figure 9:
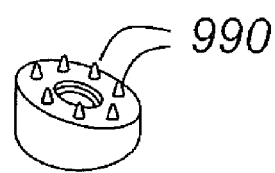
FIG. 9 shows an alternative embodiment of a nut applicable to the invention, including fixation spikes.
Figure 10:
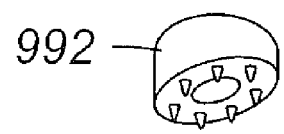
FIG. 10 shows the use of a washer according to the invention, which may be wedge-shaped and which may use fixation spikes.
Figure 11:
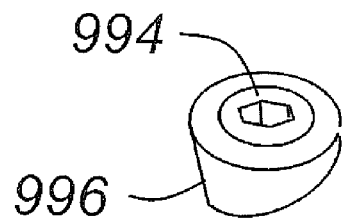
FIG. 11 is a drawing that shows the way in which a bolt head seats inside of a top nut through a click lock.

FIG. 9 is a drawing that shows an alternative nut useful in conjunction with the invention, including an optional wedge-shape and, independent of that, the use of fixation spikes 990 operative to dig into the bone, particularly during and after compression of the joint. FIG. 10 shows how the upper nut, in particular, may be replaced with a washer 992 devoid of threats. Optionally, as with the lower locking nut, the shape of the washer in FIG. 10 may be wedge-shaped or contoured to match the facet surface, and may include optional fixation spikes as well. FIG. 11 shows the way in which a bolt head 994 may seat inside of the top nut 996, and locking in position with click stops (not visible in the picture).

I claim:

1. An implant for fastening a superior facet to an inferior facet, comprising:

a first fastener portion comprising a head;

a second fastener portion configured to be connected with the first fastener portion on opposite sides of a facet joint such that a portion of the first fastener portion is configured to be positioned adjacent to one of a superior articular process and an inferior articular process of the facet joint and a portion of the second fastener portion is configured to be positioned adjacent to one of the other of an inferior articular process and a superior articular process of the facet joint so as to engage a surface of the respective articular process; and a first washer, the head of the first fastener portion received in the first washer in an assembled configuration, and wherein a bottom surface of the first washer, in an unassembled configuration, is contoured to match a surface of one of the inferior articular process and the superior articular process.

2. The implant of claim 1, wherein:
the first fastener portion comprises internal threads; and
the second fastener portion comprises external threads that are configured to engage the internal threads of the first fastener portion.

3. The implant of claim 1, wherein the second fastener portion comprises a plurality of bone fixation spikes.

4. The implant of claim 1, wherein the head comprises a bolt head.

5. The implant of claim 1, wherein the first washer comprises a threaded washer.

6. The implant of claim 1, wherein the first washer comprises a plurality of fixation spikes.

7. The implant of claim 1, further comprising a second washer configured to engage a surface of one of the inferior articular process and the superior articular process opposite from that of the first washer.

8. The implant of claim 7, wherein the second washer comprises a part of the second fastener portion.

9. The implant of claim 8, wherein the second washer comprises an integral part of the second fastener portion.

10. The implant of claim 7, wherein a surface of the second washer is contoured to match a surface of one of the inferior articular process and the superior articular process opposite from that of the first washer.

11. The implant of claim 1, wherein at least one of the first and second fastener portions is configured to be installed on a guide wire.

12. The implant of claim 11, wherein both the first and second fastener portions are configured to be installed on a guide wire.

13. The implant of claim 1, wherein the first washer is substantially wedge-shaped.

* * * * *